US008709084B2

(12) United States Patent
Glazer et al.

(10) Patent No.: US 8,709,084 B2
(45) Date of Patent: Apr. 29, 2014

(54) DEVICES FOR DELIVERING SPINAL DISC IMPLANTS

(76) Inventors: Paul A. Glazer, Chestnut Hill, MA (US); Lawrence Crainich, Charlestown, NH (US)

( * ) Notice: Subject to any disclaimer, the term of this patent is extended or adjusted under 35 U.S.C. 154(b) by 395 days.

(21) Appl. No.: 12/896,011

(22) Filed: Oct. 1, 2010

(65) Prior Publication Data

US 2011/0082554 A1    Apr. 7, 2011

Related U.S. Application Data

(60) Provisional application No. 61/248,220, filed on Oct. 2, 2009.

(51) Int. Cl.
*A61F 2/44* (2006.01)
*A61B 17/70* (2006.01)

(52) U.S. Cl.
USPC ....... 623/17.16; 606/86 A; 606/99; 623/17.11

(58) Field of Classification Search
USPC .......... 623/17.11–17.16; 606/92–94, 99, 246, 606/249
See application file for complete search history.

(56) References Cited

U.S. PATENT DOCUMENTS

| 7,223,227 | B2 | 5/2007 | Pflueger |
| 7,632,294 | B2 | 12/2009 | Milbodker et al. |
| 2003/0199979 | A1 | 10/2003 | McGuckin, Jr. |
| 2005/0060038 | A1 | 3/2005 | Lambrecht et al. |
| 2005/0070913 | A1* | 3/2005 | Milbocker et al. ............ 606/92 |
| 2005/0283246 | A1* | 12/2005 | Cauthen et al. ............ 623/17.16 |
| 2006/0247785 | A1 | 11/2006 | Gorensek et al. |
| 2006/0253198 | A1* | 11/2006 | Myint et al. ............ 623/17.12 |
| 2007/0276365 | A1 | 11/2007 | Song et al. |
| 2008/0221628 | A1 | 9/2008 | Milbocker et al. |
| 2009/0024107 | A1 | 1/2009 | Wilson et al. |

OTHER PUBLICATIONS

International Search Report and Written Opinion for corresponding PCT Application No. PCT/US2010/051074.
Xclose™ Tissue Repair System, www.anulex.com/anulex_technology/xclose.asp webpage, accessed Jul. 20, 2009.
Inclose™ Surgical Mesh System, www.anulex.com/anulex_technology/inclose_us.asp webpage, accessed Jul. 20, 2009.

* cited by examiner

*Primary Examiner* — Nicholas Woodall
(74) *Attorney, Agent, or Firm* — Edwards Wildman Palmer LLP; Joshua L. Jones; Alicia J. Esposito

(57) ABSTRACT

A spinal disc implant delivery device includes a blocking component having opposed distal and proximal ends. The proximal end of the blocking component includes an anchor member configured and adapted for movement between an undeployed position in which the anchor member can pass into and out of an opening in a disc annulus, and a deployed position in which the anchor member anchors the blocking component to the opening of the disc annulus. In the deployed position, the anchor member is configured to prevent extrusion of implant material from the opening of the disc annuls. An implant delivery needle is located radially within the blocking component and has opposed proximal and distal ends. The needle is configured to deliver implant material from the distal end thereof to an interior of a disc annulus.

9 Claims, 17 Drawing Sheets

DEVICES FOR DELIVERING SPINAL DISC IMPLANTS

CROSS-REFERENCE TO RELATED APPLICATIONS

This application claims priority to U.S. Provisional Patent Application No. 61/248,220, filed Oct. 2, 2009, which is incorporated by reference herein in its entirety.

BACKGROUND OF THE INVENTION

1. Field of the Invention

The present invention relates to methods and devices for treating spinal conditions, and more particularly, to methods and devices for modifying intervertebral disc tissue.

2. Description of Related Art

A variety of devices and methods are known in the art for treating pain in the human spine. Of such devices, many are directed to relieving pain arising from intervertebral disc abnormalities. Intervertebral disc abnormalities are common in the population and cause considerable pain, particularly if they affect adjacent nerves. Disc abnormalities result from trauma, wear, metabolic disorders and the aging process and include degenerative discs, localized tears or fissures in the annulus fibrosus, localized disc herniations with contained or escaped extrusions, and chronic, circumferential bulging discs. Disc fissures occur as a degeneration of fibrous components of the annulus fibrosus. Rather minor activities such as sneezing, bending or simple attrition can tear degenerated annulus fibers and create a fissure. The fissures may be further complicated by extrusion of nucleus pulposus material into or beyond the annulus fibrosus. Difficulties can still present even when there is no visible extrusion, due to biochemicals within the disc irritating surrounding structures and nerves.

A contained disc herniation is not associated with free nucleus fragments migrating to the spinal canal. However, a contained disc herniation can still protrude and irritate surrounding structures, for example by applying pressure to spinal nerves. Escaped nucleus pulposus can chemically irritate neural structures. Current treatment methods include reduction of pressure on the annulus by removing some of the interior nucleus pulposus material by percutaneous nucleotomy. Complications include disc space infection, nerve root injury, hematoma formation, instability of the adjacent vertebrae and collapse of the disc from decrease in height. It has been proposed to treat weakening due to nucleus pulposus deficiency by inserting preformed hydrogel implants.

More recently, delivery of in situ curing liquids to form a solid prosthetic in the nucleus of a disc have been disclosed. The fluid form of these implants enables access to the spine in a minimally invasive manner, and includes procedures for restoring structural integrity to vertebral bodies. There are a variety of injectable biomaterials known in the art including: cross-linkable silk elastin copolymer, protein hydrogel, polyurethane-filled balloons, collagen-PEG, chitosan, and other polymers.

Delivery of an in situ forming prosthetic to the nuclear space requires constructing a passageway into the nucleus and removal of the nucleus fibrosus, in total or in part. The passageway is usually made through the annulus, especially when part of the annulus needs to be removed to correct a pathological condition. Whether the passageway is through the annulus or elsewhere, for example, through the vertebral body, there is a risk of the formed nucleus prosthetic extruding out through the passageway into which it is introduced. Nucleus prosthetic extrusion can affect the surrounding nerves adversely. Methods of blocking a passageway made through the annulus include, for example, enclosing the prosthetic entirely inside of an enveloping sheath. Still other methods of preventing nuclear prosthetic extrusion include delivering a preformed prosthetic in a reduced state, which when introduced into the body increases in volume.

U.S. Patent Application Publication No. 2009/0024107, to Wilson et al., describes a device for blocking a passageway made through the annulus to prevent extrusion of implant material. A catheter balloon is introduced into the annulus opening flush with the interior space of the annulus while implant material is injected through an axially located catheter running through the interior of the catheter balloon. This technique can block extrusion of the implant material through the opening of the annulus, however it does not provide a positive anchor of the delivery apparatus. Therefore, it is necessary for the user of the device to devote constant attention to prevent accidental removal of the catheter balloon during the procedure. If the device is accidentally removed from the annulus during the procedure, not only will there be difficulty in repositioning the device at the opening of the annulus, but implant material can freely exit the opening of the annulus, giving rise to further complications.

This typically means that one hand of the user is constantly tied up just to maintain the position of the device. This is a problem, when for example, two hands are required to attach a syringe of implant material to the applicator during a procedure. Even when the user manages to maintain the position of the device using one hand, difficulties can arise if, for example, the user's other hand is also tied up with actuating the injection of the implant. In such situations, the user will not have any hand free for other necessary tasks that may arise during the procedure.

The conventional methods and systems have generally been considered satisfactory for their intended purpose. However, there still remains a continued need in the art for methods and devices that can provide improved blocking of disc implant material from extrusion out the opening of a vertebral disc annulus while providing improved anchoring of a delivery device to the opening of the annulus. There also remains a need in the art for such methods and devices that are easy to make and use. The present invention provides a solution for these problems.

SUMMARY OF THE INVENTION

The subject invention is directed to a new and useful spinal disc implant delivery device. The device includes a blocking component having opposed distal and proximal ends. The proximal end of the blocking component includes an anchor member configured and adapted for movement between an undeployed position in which the anchor member can pass into and out of an opening in a disc annulus, and a deployed position in which the anchor member anchors the blocking component to the opening of the disc annulus. In the deployed position, the anchor member is configured to prevent extrusion of implant material from the opening of the disc annuls. An implant delivery needle is located radially within the blocking component and has opposed proximal and distal ends. The needle is configured to deliver implant material from the distal end thereof to an interior of a disc annulus.

In accordance with certain embodiments, the implant delivery needle is moveable relative to the blocking component in an axial direction. A pressure sensor can be mounted to at least one of the blocking component and the implant delivery needle, or any other suitable location for monitoring pressure within a disc annulus during an implant procedure.

The anchor member can include a mesh portion that is biased toward the deployed position. The mesh portion can include a membrane lining to prevent extrusion of implant material through the mesh portion.

In certain embodiments, the anchor member includes a catheter balloon configured and adapted to inflate into the deployed position within an interior of a disc annulus to prevent withdrawal of the blocking component from the disc annulus. The blocking component can include a catheter having opposed proximal and distal ends, wherein the catheter balloon is attached to the catheter by a ferrule mounted to the catheter. The ferrule can be mounted at the distal end of the catheter. It is also contemplated that the catheter balloon can include a flexible tube with a distal end thereof folded radially inward and overlapping a radially outward portion of the flexible tube, with the distal end of the flexible tube being mounted to the catheter proximate the distal end of the catheter.

The invention also provides a method of delivering a spinal disc implant. The method includes introducing a blocking device into an opening of a spinal disc annulus, the blocking device including an anchor member proximate a distal end thereof. A step is included for extending the anchor member of the blocking device into an interior of the disc annulus. The method also includes actuating the anchor member from an undeployed position in which the anchor member can pass into and out of an opening in the disc annulus, to a deployed position in which the anchor member anchors the blocking component to the interior of the disc annulus.

In certain embodiments, the method includes introducing spinal disc implant material into the interior of the annulus and using the anchor member to block extrusion of the implant material through the opening of the annulus. It is also contemplated that the step of actuating can include positioning a proximal surface of the anchor member against a wall of the interior of the disc annulus adjacent the opening therein. The method can include leaving the anchor member in the deployed position as the implant material cures within the interior of the annulus. It is also contemplated that the method can include moving a distal end of a delivery needle into the interior space of the annulus to deliver the implant material, wherein the delivery needle is moved through an interior passage of the blocking device.

In accordance with certain embodiments, the anchor member includes a catheter balloon, and the step of actuating the anchor member includes inflating the catheter balloon within the interior of the annulus. The method can include compressing the inflated catheter balloon with implant material. It is also contemplated that the method can include deflating the catheter balloon and withdrawing the blocking device from the opening of the disc annulus. It is also contemplated that the anchor member can include a mesh portion biased radially outward toward the deployed position, wherein the step of actuating the anchor member includes advancing the mesh portion beyond a delivery catheter holding the mesh portion in the undeployed position. The method can include returning the mesh portion to the undeployed position for withdrawal from the annulus by urging the mesh portion into the delivery catheter. A step can also be included for monitoring pressure in the interior of the disc annulus using a pressure sensor operatively connected to the blocking device.

The invention also provides an implant delivery device with a blocking component having opposed distal and proximal ends. The proximal end of the blocking component includes a seal member configured and adapted for movement between an undeployed position in which the seal member can pass into and out of an opening in a surgical treatment site, and a deployed position in which the seal member seals the opening in the surgical treatment site to reduce or prevent extrusion of implant material from the opening in the surgical treatment site. An implant delivery needle is located radially within the blocking component and has opposed proximal and distal ends. The needle is configured to deliver implant material from the distal end thereof to an area inside the opening in the surgical treatment site. The seal member can be configured to seal against an opening in a surgical site for kyphoplasty, vertebroplasty, open or percutaneous nucleotomy or discectomy, or any other suitable procedure.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION OF THE PREFERRED EMBODIMENTS

Figure 1:
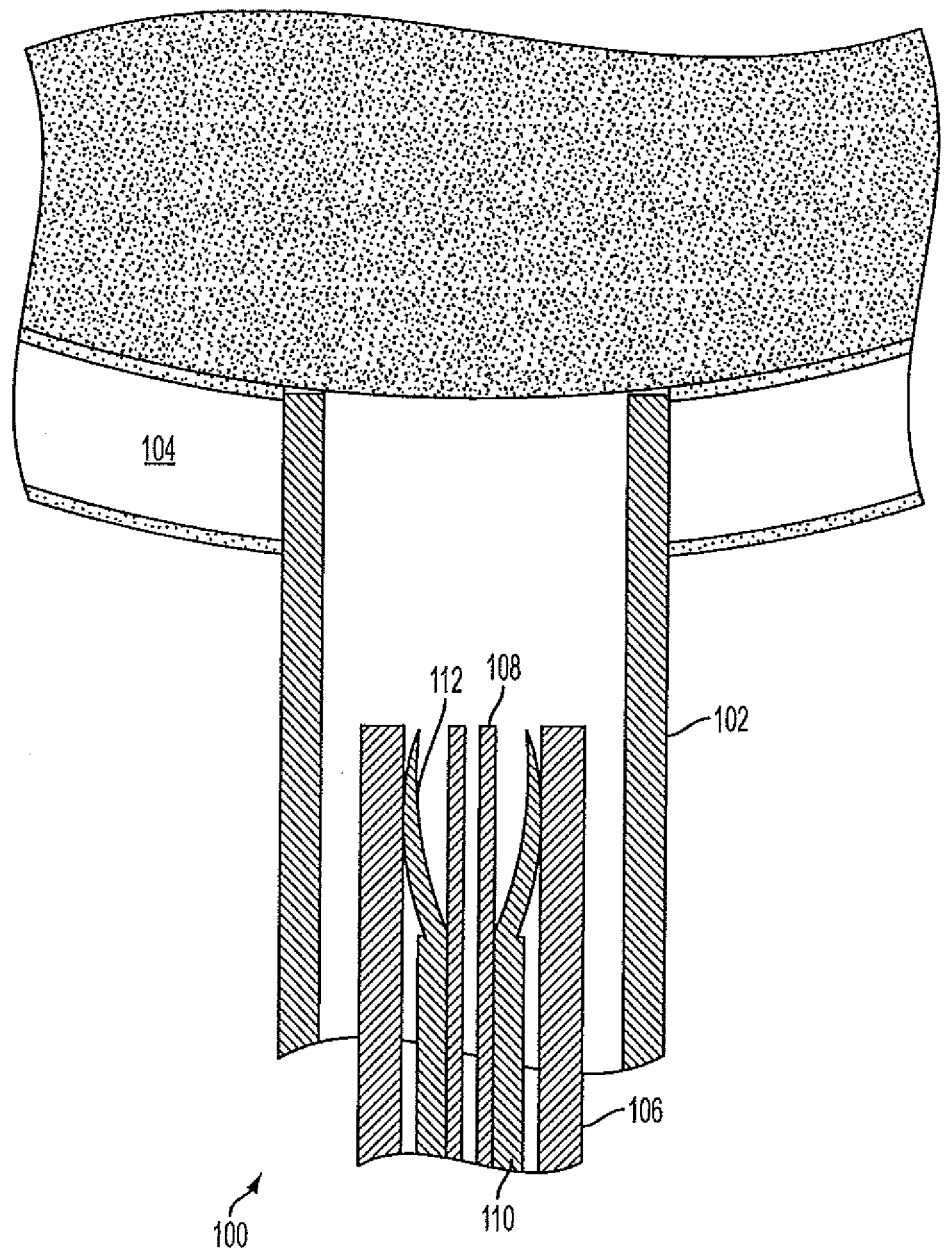
FIG. 1 is a schematic cross-sectional side elevation view of an exemplary embodiment of a spinal implant delivery device constructed in accordance with the present invention, showing the device being introduced through a cannula to the interior space of a vertebral disc annulus.

Reference will now be made to the drawings wherein like reference numerals identify similar structural features or aspects of the subject invention. For purposes of explanation and illustration, and not limitation, a partial view of an exemplary embodiment of the spinal implant delivery device in accordance with the invention is shown in FIG. 1 and is designated generally by reference character 100. Other embodiments of spinal implant delivery devices in accordance with the invention, or aspects thereof, are provided in FIGS. 2-21, as will be described. The systems and methods of the invention can be used to anchor spinal implant delivery instruments and to block spinal implant material from extruding into undesirable locations.

Referring now to FIG. 1, a cannula 102 is introduced through the annulus 104 of a spinal disc by conventional percutaneous methods, such as by first placing a percutaneous introducer wire through annulus 104 and creating an opening for cannula 102 by using an obturator introduced over the introducer wire. The nucleus of the disc, or a portion thereof, can be removed by conventional techniques by instruments such as surgical razor blades introduced to the interior of annulus 104 via cannula 102. Examples of preliminary steps for reaching the state shown in FIG. 1 are described in general in U.S. Patent Application Publication No. 2009/0024107, to Wilson et al., which is incorporated by reference herein in its entirety.

FIG. 1 shows annulus 104 with cannula 102 already introduced, and with the nucleus already removed, as indicated by the texture in FIG. 1. Delivery catheter 106 is advanced through cannula 102 into the interior of annulus 104. Catheter 106 contains an implant delivery needle 108 and a blocking component 110. The distal end of blocking component 110 includes a mesh portion 112 that is biased outward against the inner surface of catheter 106.

Figure 2:
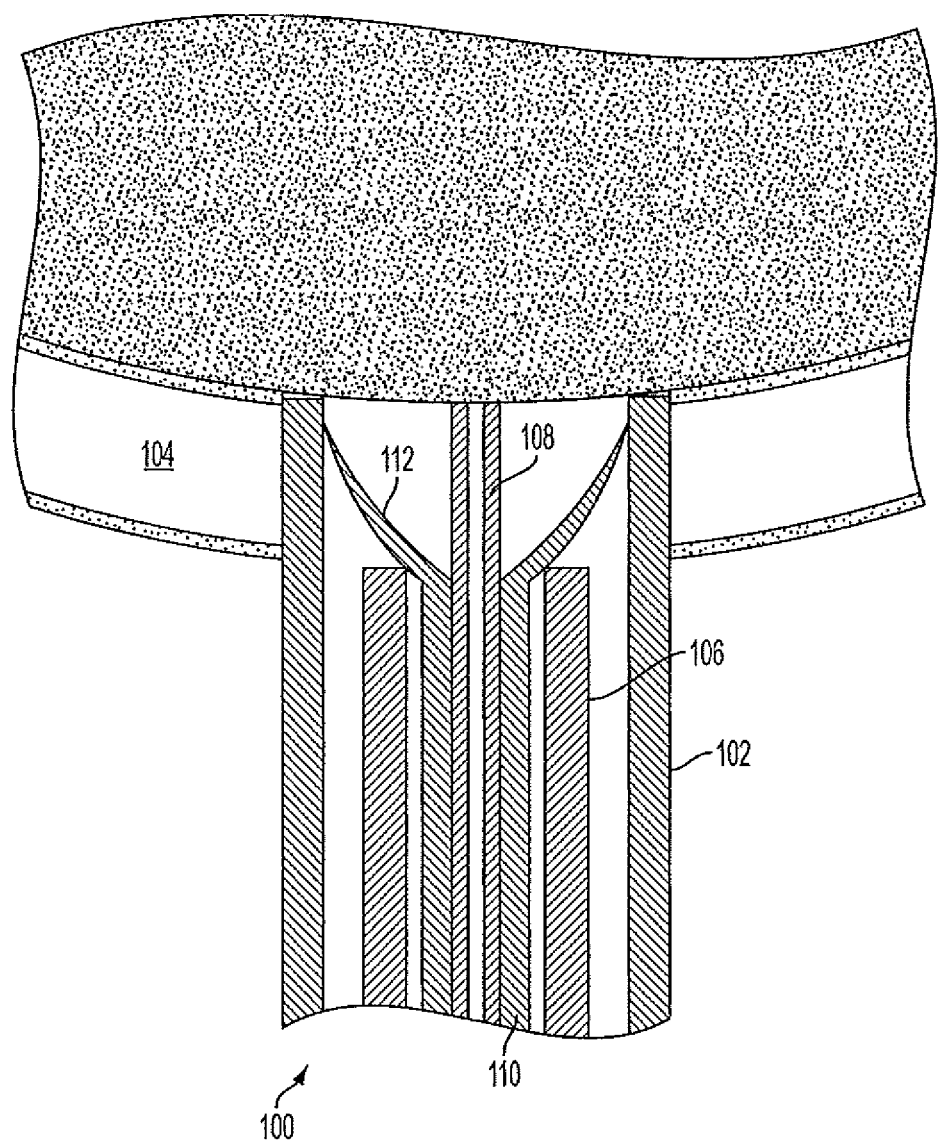
FIG. 2 is a schematic cross-sectional side elevation view of the device of FIG. 1, showing the anchor member of the device expanded out of the delivery catheter.

Referring now to FIG. 2, needle 108 and blocking component 110 are shown in a position advanced beyond the end of catheter 106. Mesh portion 112 of blocking component 110 is shown beginning to open, and in this position it is biased against the inner surface of cannula 102. It is also possible to advance needle 108 and blocking component 110 out of catheter 106 with catheter 106 advanced beyond the end of cannula 102.

Figure 3:
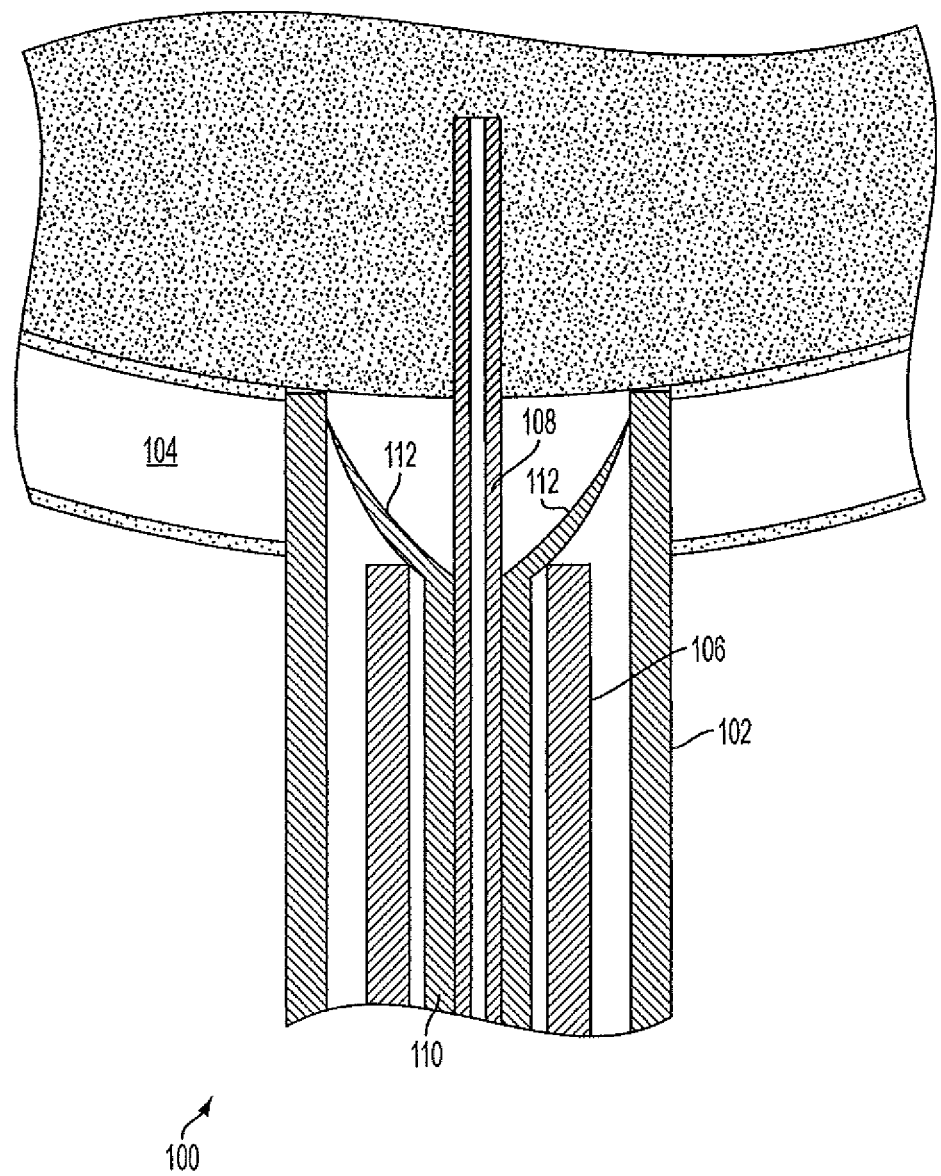
FIG. 3 is a schematic cross-sectional side elevation view of the device of FIG. 1, showing the implant delivery needle extended into the interior space of the annulus.
Figure 4:
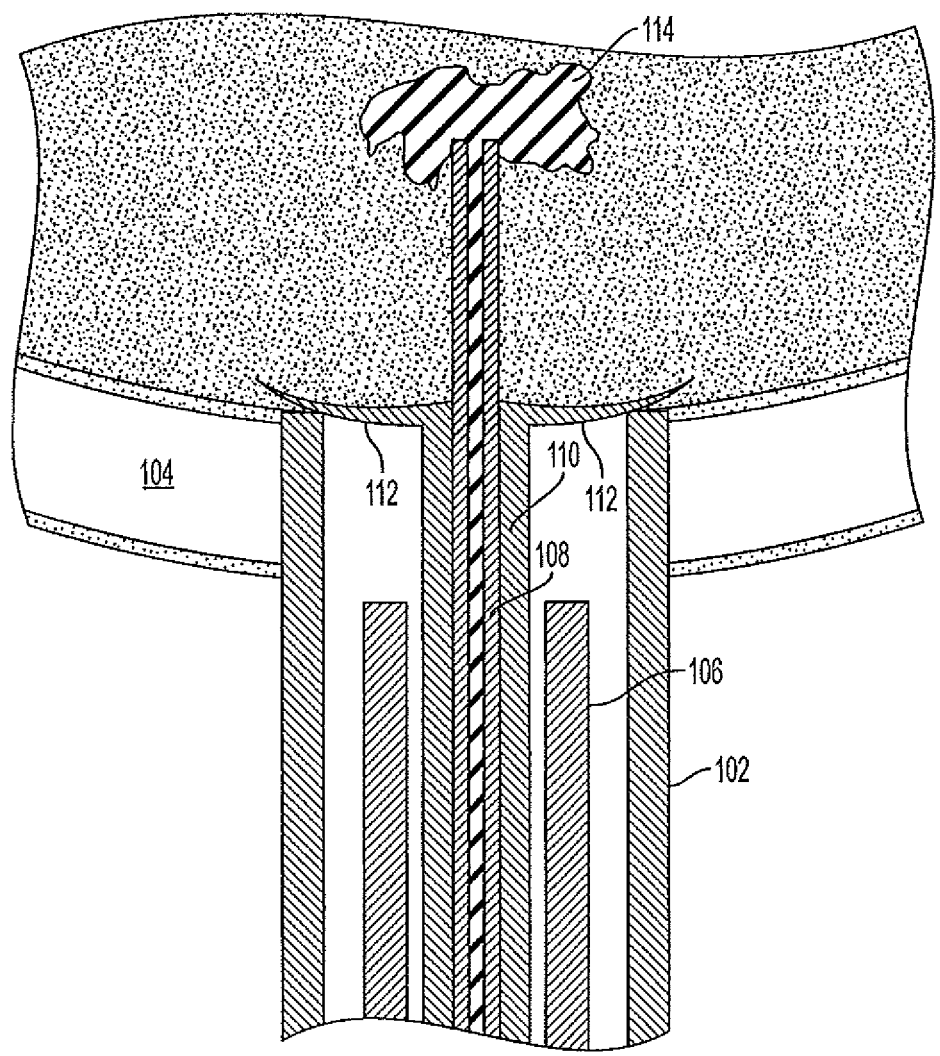
FIG. 4 is a schematic cross-sectional side elevation view of the device of FIG. 1, showing the anchor member of the device anchored in the interior space of the annulus while implant material is injected through the needle.

As shown in FIG. 3, needle 108 can be advanced independent of blocking component 110. From the position shown in FIG. 3, if blocking component 110 is advanced beyond cannula 102, the biasing force of mesh portion 112 allows full opening of blocking component 110 as shown in FIG. 4. Mesh portion 112 is made of a mesh material and in its expanded state within annulus 104, it blocks the opening of annulus 104 during injection of disk implant material 114. If the mesh size is too great to prevent a given implant material passing therethrough, then the mesh can advantageously be lined with a thin, stretchable liner made of c-flex polymer, or any other suitable material.

Figure 5:
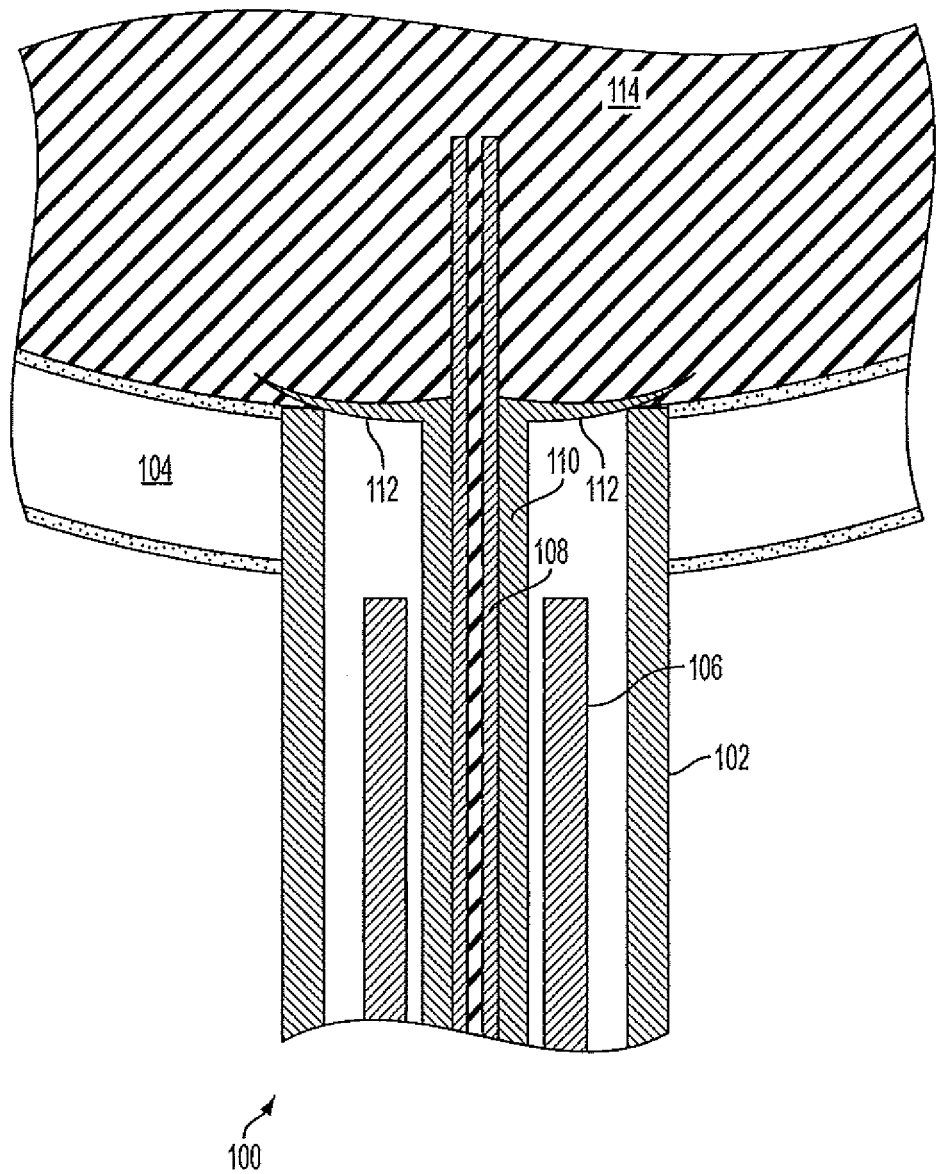
FIG. 5 is a schematic cross-sectional side elevation view of the device of FIG. 1, showing the interior space of the annulus filled with implant material with the anchor member blocking extrusion of the implant material from the opening of the annulus.
Figure 6:
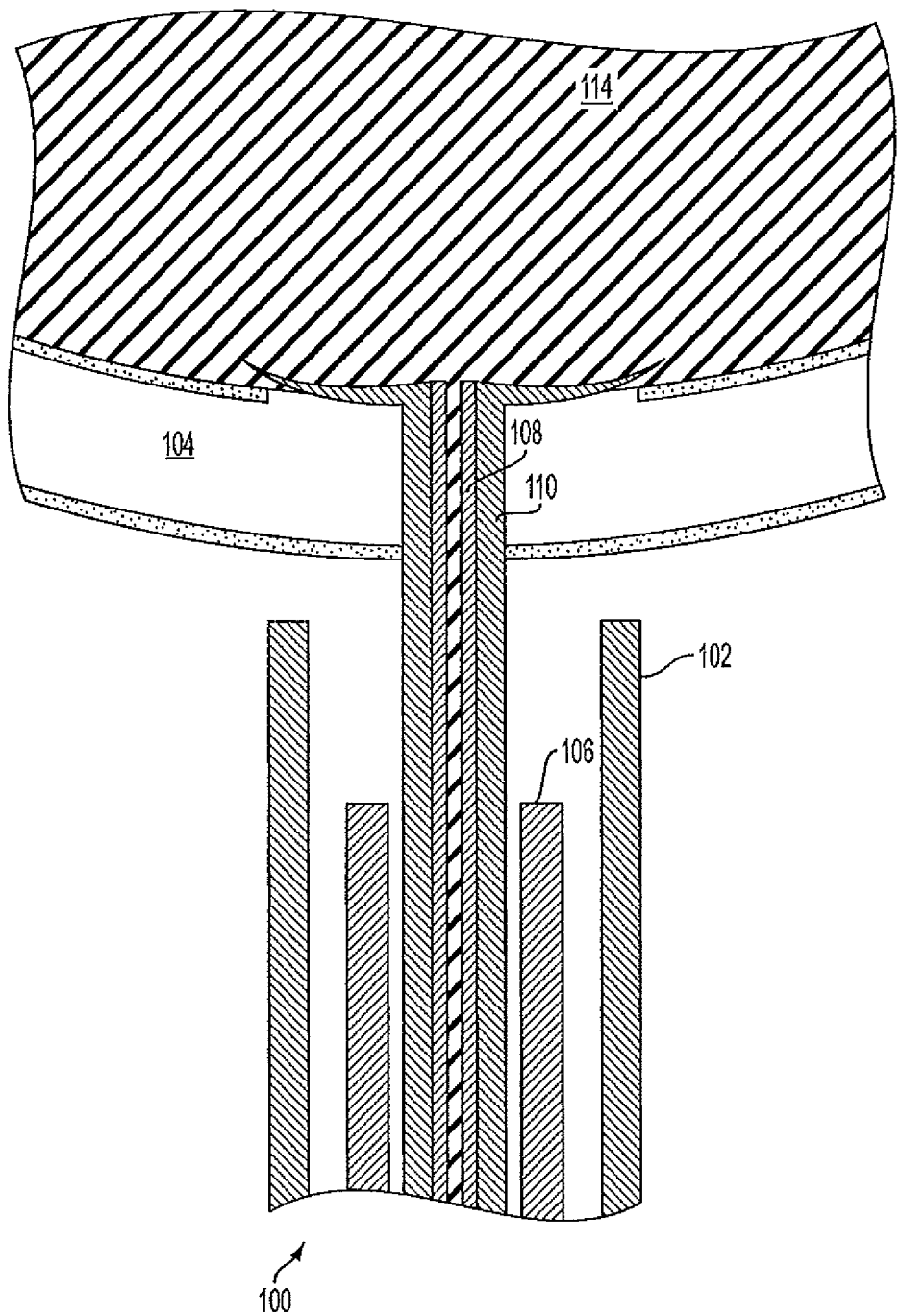
FIG. 6 is a schematic cross-sectional side elevation view of the device of FIG. 1, showing the catheter withdrawn from the opening of the annulus with the anchor member holding the device in place.

It is important to block implant material 114 from extruding beyond the opening created in annulus 104 during the procedure as such extrusions can have detrimental effects on the surrounding nerves. FIG. 5 shows the nucleus area of annulus 104 filled with implant material 114, and because the expanded mesh portion 112 of blocking component HQ covers the opening in annulus 104, implant material 114 is confined in the desired location. As shown in FIGS. 5-6, a proximal surface of anchor member 112 is positioned against a wall of the interior of annulus 104 adjacent the opening therein, and since anchor member 112 is larger than the opening in annulus 104, anchor member 112 retains blocking component 110 at the opening of annulus 104.

With reference now to FIG. 6, cannula 102 and catheter 106 can be withdrawn leaving needle 108 and blocking component 110 in place, and allowing annulus 104 to close in around blocking component 110. Blocking component 110 can be kept in place as implant material 114 cures. This is beneficial because many typical implant materials expand as they cure and without blocking the opening in annulus 104, implant material 114 would tend to extrude from annulus 104 as discussed above.

Figure 7:
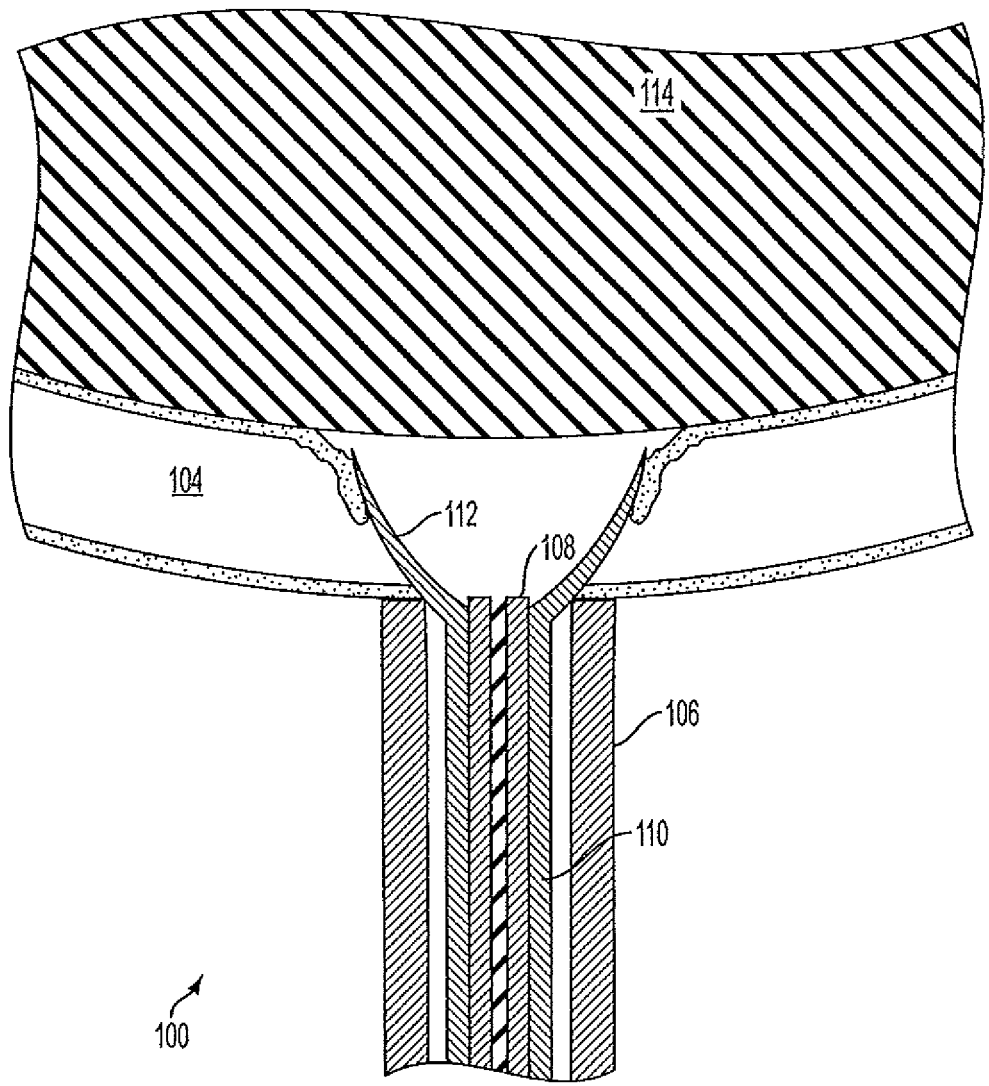
FIG. 7 is a schematic cross-sectional side elevation view of the device of FIG. 1, showing removal of the anchor member from the annulus after the implant material is cured.

FIG. 7 shows implant material 114 in a cured state, as indicated by hatching. With implant material 114 set or cured, catheter 106 can be reintroduced over blocking component 110 for removal of blocking component 110 from annulus 104. Optionally, catheter 106 can be left in place while implant material 114 cures rather than being removed and then later replaced. As blocking component 110 is withdrawn into catheter 106, the inner wall of catheter 106 causes mesh portion 112 of blocking component 110 to contract as it is removed from the opening in annulus 104.

Figure 8:
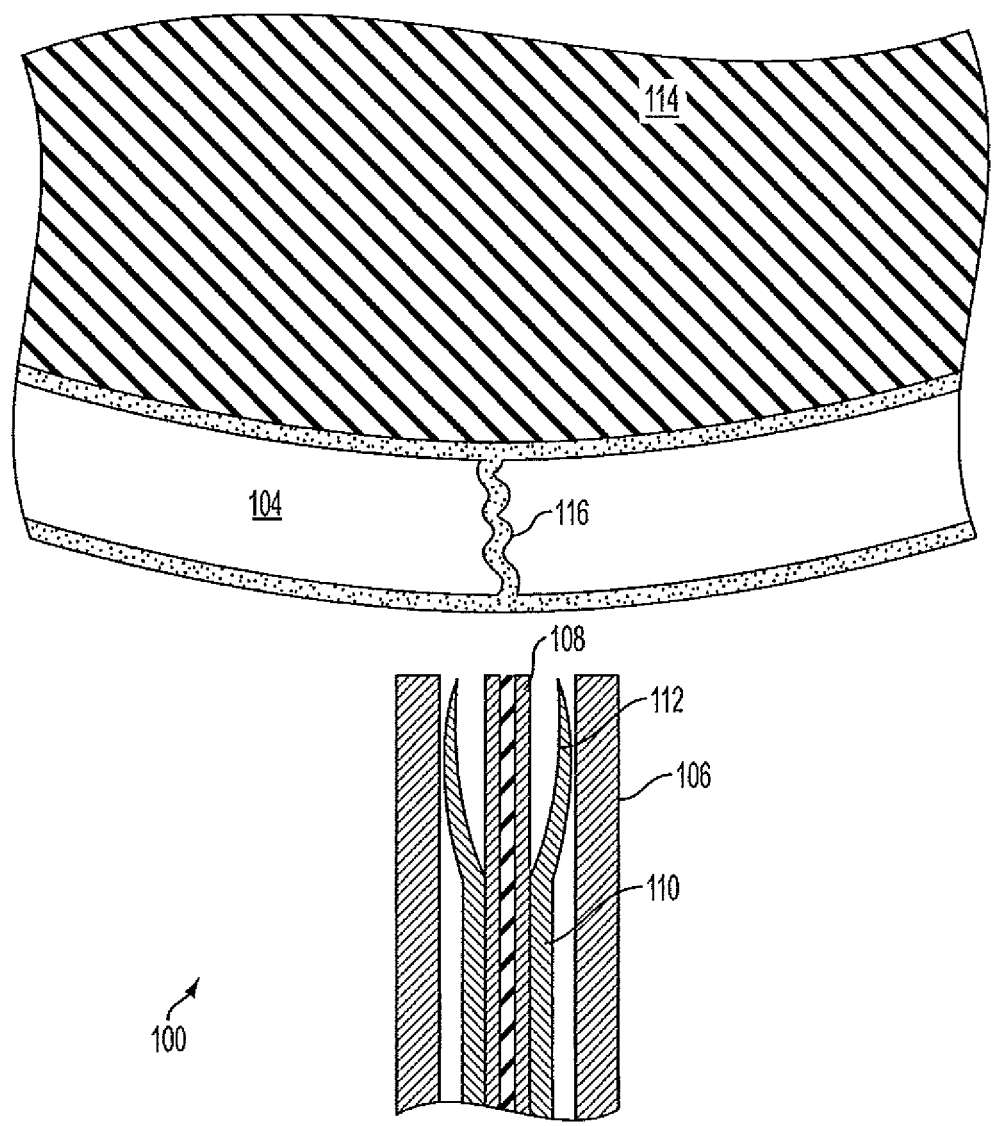
FIG. 8 is a schematic cross-sectional side elevation view of the device of FIG. 1, showing the device withdrawn from the disc annulus with the opening of the disc annulus reapproximated.

Referring now to FIG. 8, with blocking component 110 fully retracted within catheter 106, catheter 106, blocking component 110, and needle 108 can be removed from annulus 104. Conventional methods can be used as needed to reapproximate the opening in annulus 104, as indicated by reference character 116.

Blocking component 110 not only blocks implant material 114 from protruding beyond the opening in annulus 104, it also maintains or anchors its position as well as that of needle 108 within annulus 104 during the injection and curing of implant material 114. Typical previously known implant devices require a surgeon to maintain the position manually using at least one hand, which presents a significant challenge since it takes two hands to attach the syringe of implant material to the applicator. Blocking component 110 frees up at least one hand for the surgeon for as much time as needed without the concern of needle 108 or blocking component 110 losing position. In short, by anchoring device 100 in place, blocking component 110 allows for greater ease of application of implant material.

Device 100 can be used to deliver implant material through typical posterior approaches, anterior approaches, or by any other suitable approach. Pressure monitoring instruments can be included on needle 108 and/or blocking component 110 to allow monitoring of pressure within annulus 104 during disc repair.

While device 100 has been described above in the exemplary context of delivering spinal disc implants, there are other applications to which such devices are well suited. Another exemplary application of such devices is in the delivery of bone-forming substances such as bone morphogenic protein ("BMP") used to stimulate bone growth. Such materials can be used, for example, to help seal the opening in annulus 104 after the procedure described above. Blocking component 110 can be positioned to prevent leakage of the protein materials onto adjacent boney structures. Leakage of the protein materials could lead to unwanted bone growth, which could result in interference with nerves if used in the spinal region, for example.

It is also possible that mesh portion 112 of blocking component 110 can be configured to be detached from blocking component 110. This would allow blocking component 110 to be left in place within annulus 104 after implant material 114 is injected. Another aspect of the invention is that the implant material 114 can be delivered in a fenestrated collagen bag, which would keep implant material 114 from leaking or protruding beyond annulus 104, and which would also allow for implant material 114 to adhere to annulus 104.

Figure 9:
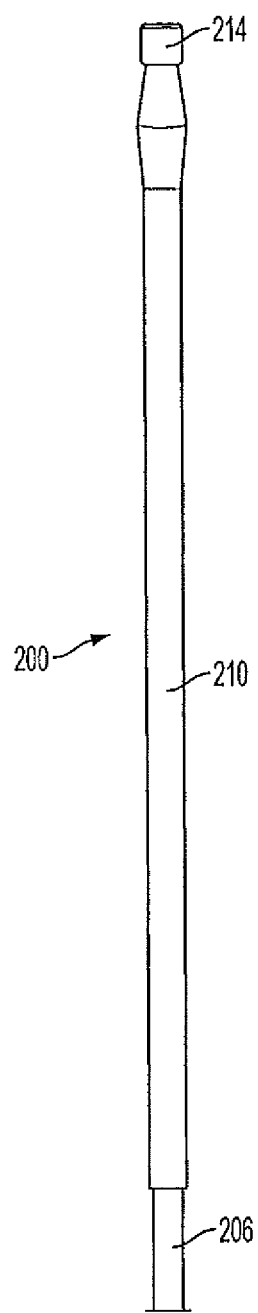
FIG. 9 is a side elevation view of another exemplary embodiment of a spinal implant delivery device constructed in accordance with the present invention, showing the distal end of the device and the anchor member.

With reference now to FIG. 9, another embodiment of a spinal implant delivery device 200 is shown. Device 200 includes a catheter 206 that is surrounded at least near its distal end with a blocking component 210 that is flexible. In FIG. 9, a portion of blocking component 210 is shown cut away to reveal catheter 206. A ferrule 214 clamps the end of blocking component 210 to catheter 206.

Figure 10:
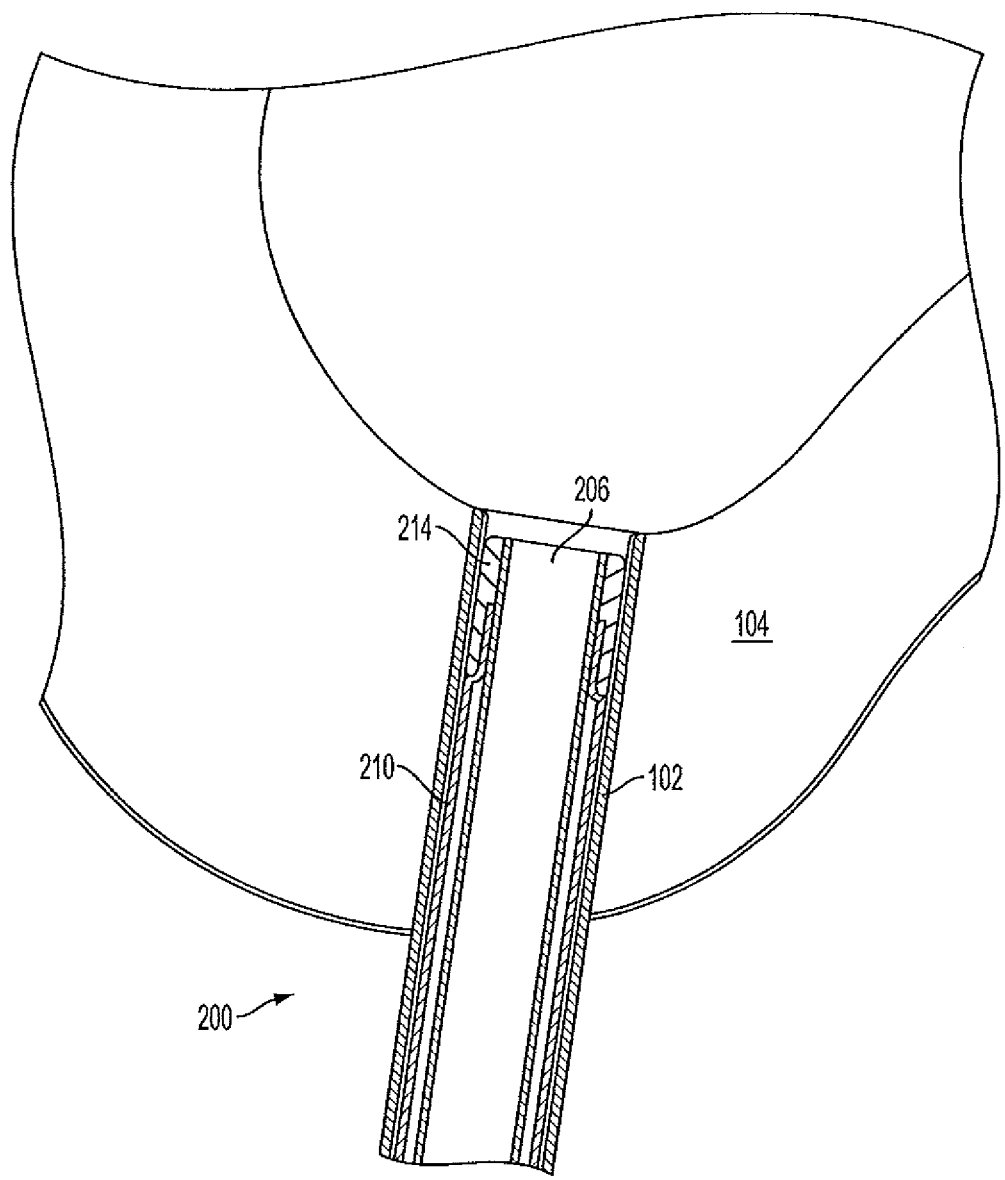
FIG. 10 is a cross-sectional side elevation view of a portion of the device of FIG. 9, showing the device being introduced through a catheter into an interior space of a disc annulus.

Referring now to FIG. 10, device 200 can be introduced to the interior of an annulus 104 by way of a cannula 102 in much the same manner as device 100 described above. FIG. 10 shows device 200 already introduced at the interior of annulus 104, which already has the nucleus removed. The center diameter of catheter 206 is sized to admit other instruments therethrough to access the disc interior for removing the nucleus and injecting the implant, much as described above with respect to device 100. A needle such as needle 108, or any other suitable delivery device, can be introduced to the interior of annulus 104 through the central passage of catheter 206, much as described above with respect to device 100.

Figure 11:
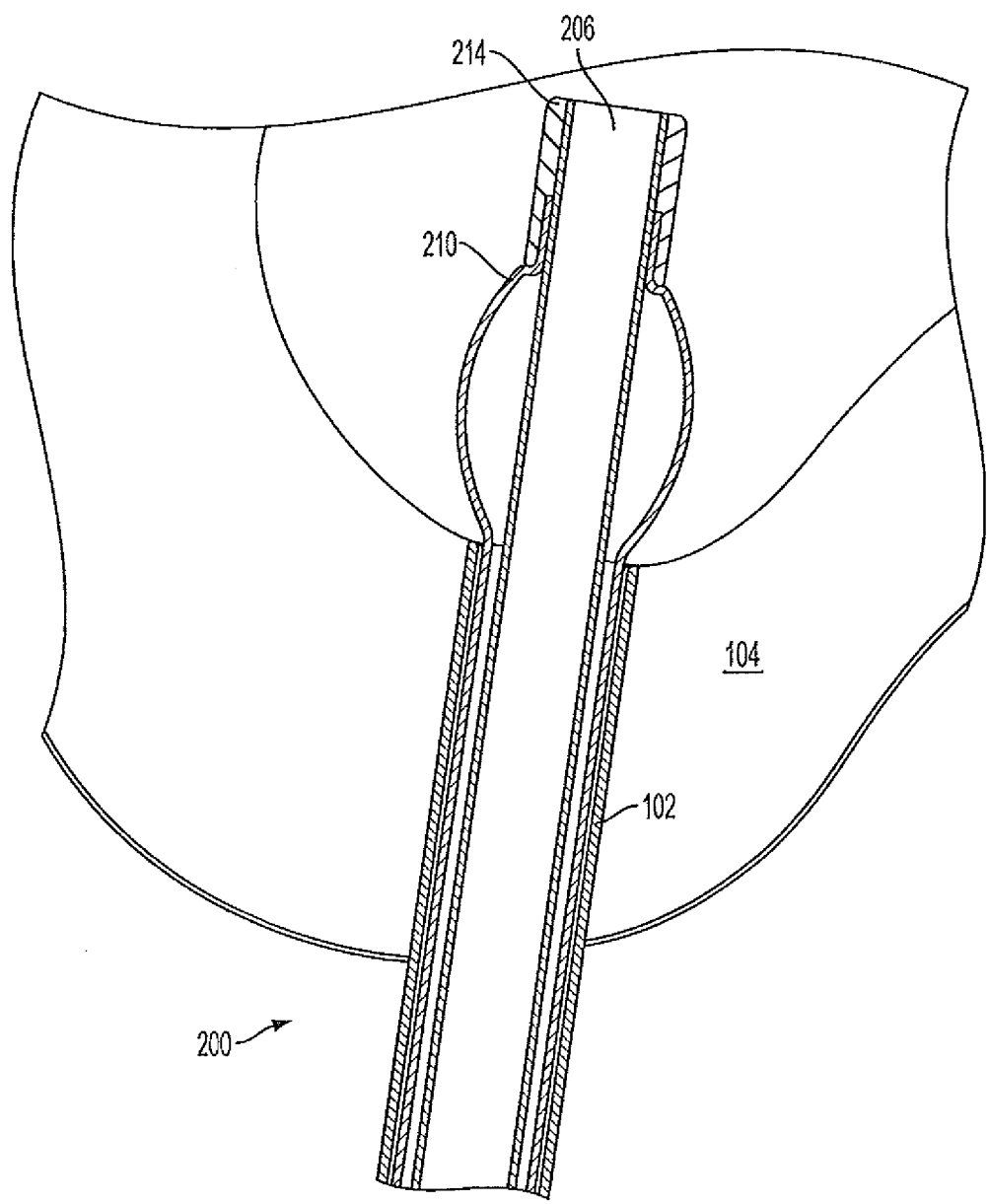
FIG. 11 is a cross-sectional side elevation view of a portion of the device of FIG. 9, showing the device extended into the interior of the annulus with a portion of the anchor member exposed beyond the end of the catheter.
Figure 12:
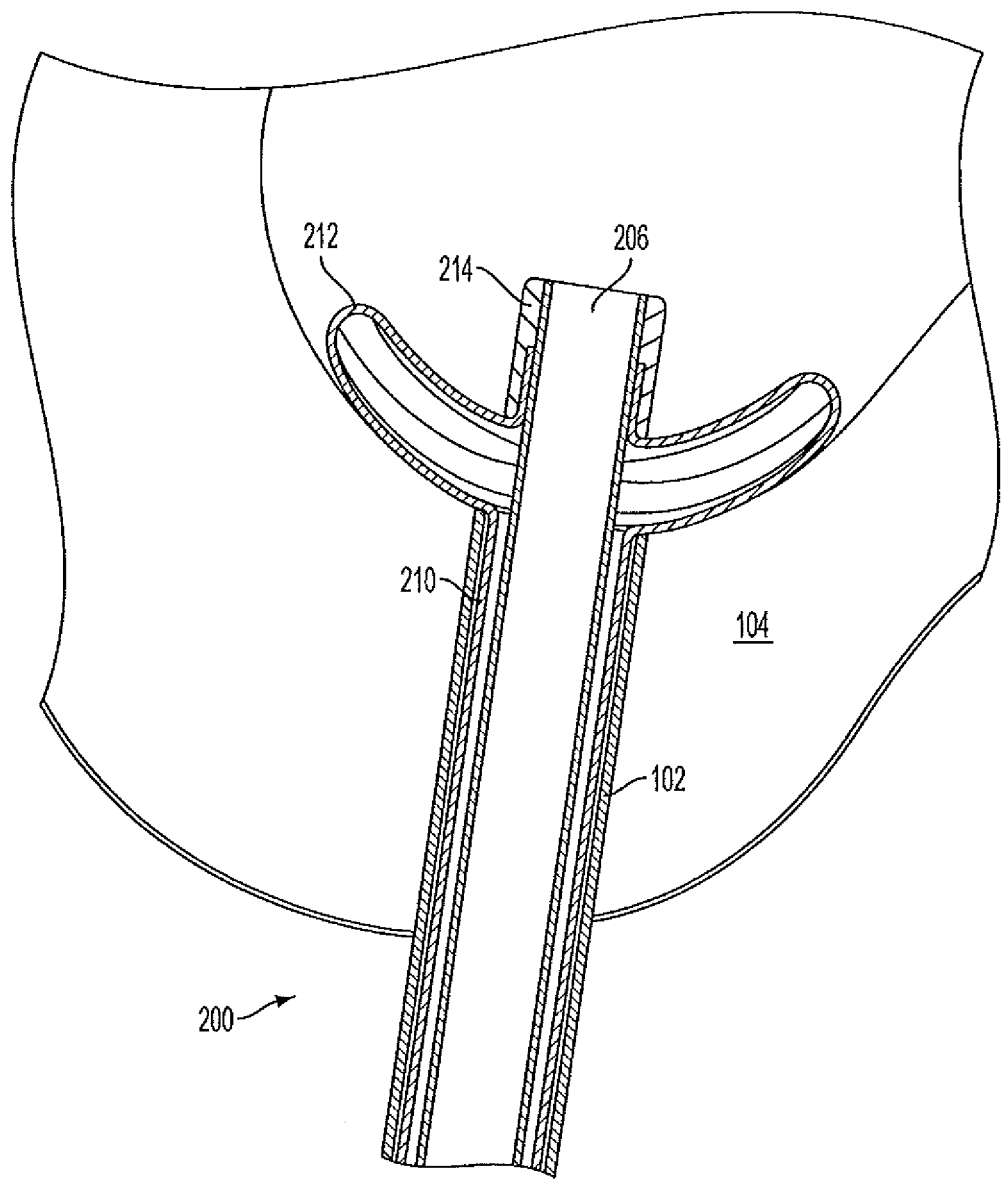
FIG. 12 is a cross-sectional side elevation view of a portion of the device of FIG. 9, showing the anchor member expanded to block implant material from extruding out of the annulus opening and to anchor the device in place.

Prior to injecting an implant into the interior of annulus 104, device 200 can be used to seal the opening of annulus 104. FIG. 11 shows device 200 extended beyond the end of cannula 102 so that ferrule 214 and a portion of blocking component 210 are exposed to the interior space of annulus 104. In this position, the distal end portion of blocking device 210 can be inflated to serve as an anchor member, as indicated in FIG. 12, by using an inflation fluid such as air or any other suitable gas or liquid. The inflated anchor member portion of blocking component 210 forms a catheter balloon 212 within the interior space of annulus 104. Catheter balloon 212 serves to anchor device 200 in position during the implant procedure so that device 200 cannot accidentally be withdrawn from annulus 104. This also seals the opening of annulus 104 from implant material leaking therethrough, much as described above with respect to device 100.

As shown in FIG. 12, a proximal surface of catheter balloon 212 is positioned against a wall of the interior of annulus 104 adjacent the opening therein, and since catheter balloon 212 is larger than the opening in annulus 104, catheter balloon 212 retains blocking component 210 at the opening of annulus 104. When it is desirable to remove device 200, catheter balloon 212 can be deflated and device 200 can be withdrawn from annulus 104.

Figure 13:
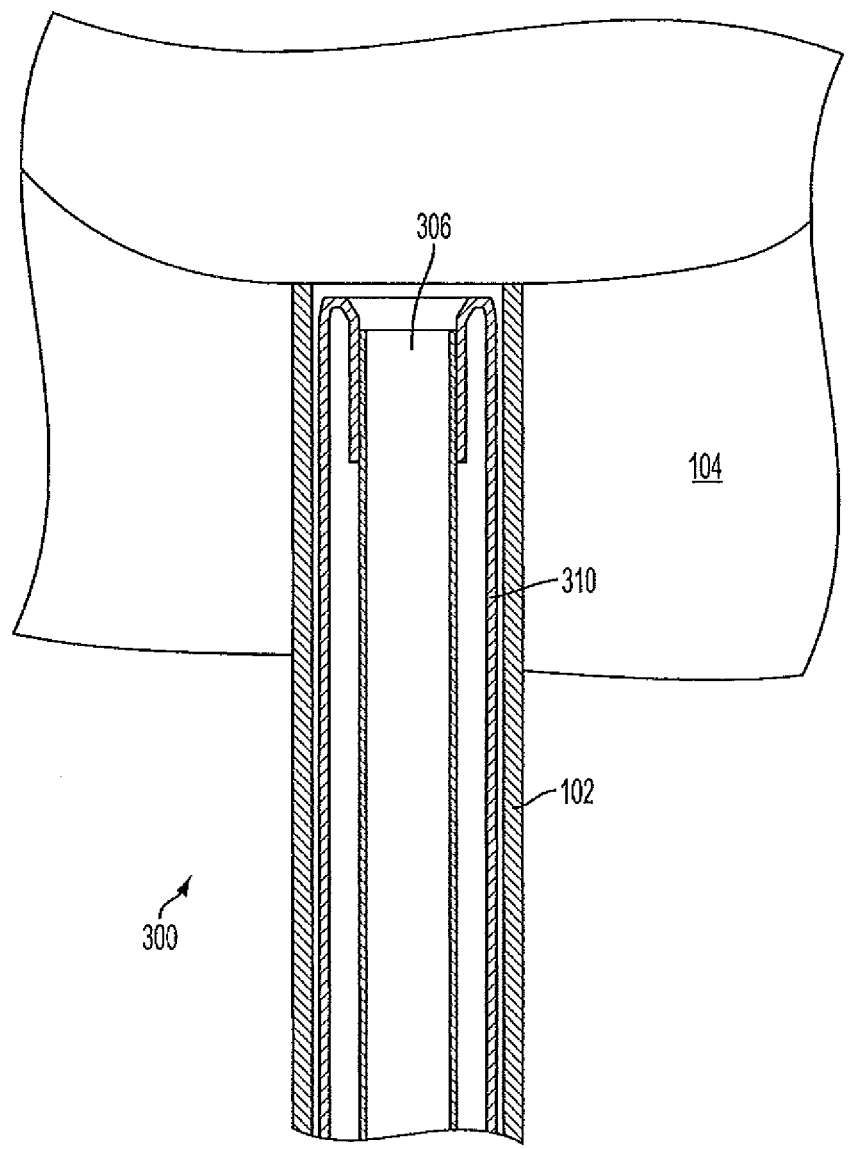
FIG. 13 is a cross-sectional side elevation view of a portion of another exemplary embodiment of a spinal implant delivery device constructed in accordance with the present invention, showing the device being introduced through a catheter into an interior space of a disc annulus.

With reference now to FIGS. 13-21, another embodiment of a device 300 in accordance with the invention is shown. Device 300 includes a flexible blocking component 310 much like blocking component 210 described above, except for the attachment to the respective catheter. Instead of being connected by a ferrule, blocking component 310 is directly attached by any suitable means to catheter 306 with blocking component 310 folded back over its own distal end, as shown in FIG. 13.

Figure 14:
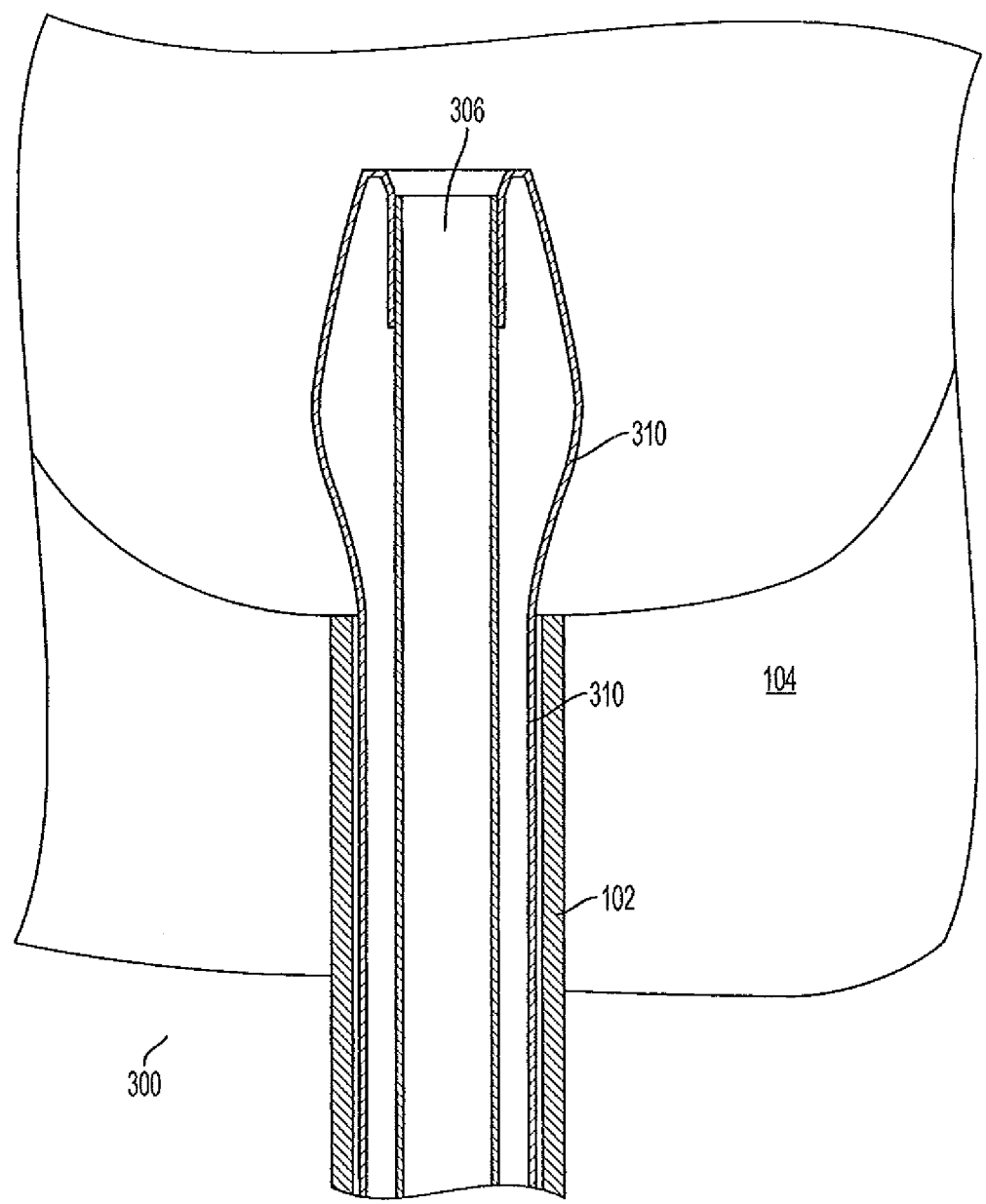
FIG. 14 is a cross-sectional side elevation view of a portion of the device of FIG. 13, showing the device extended into the interior of the annulus with a portion of the anchor member exposed beyond the end of the catheter.
Figure 15:
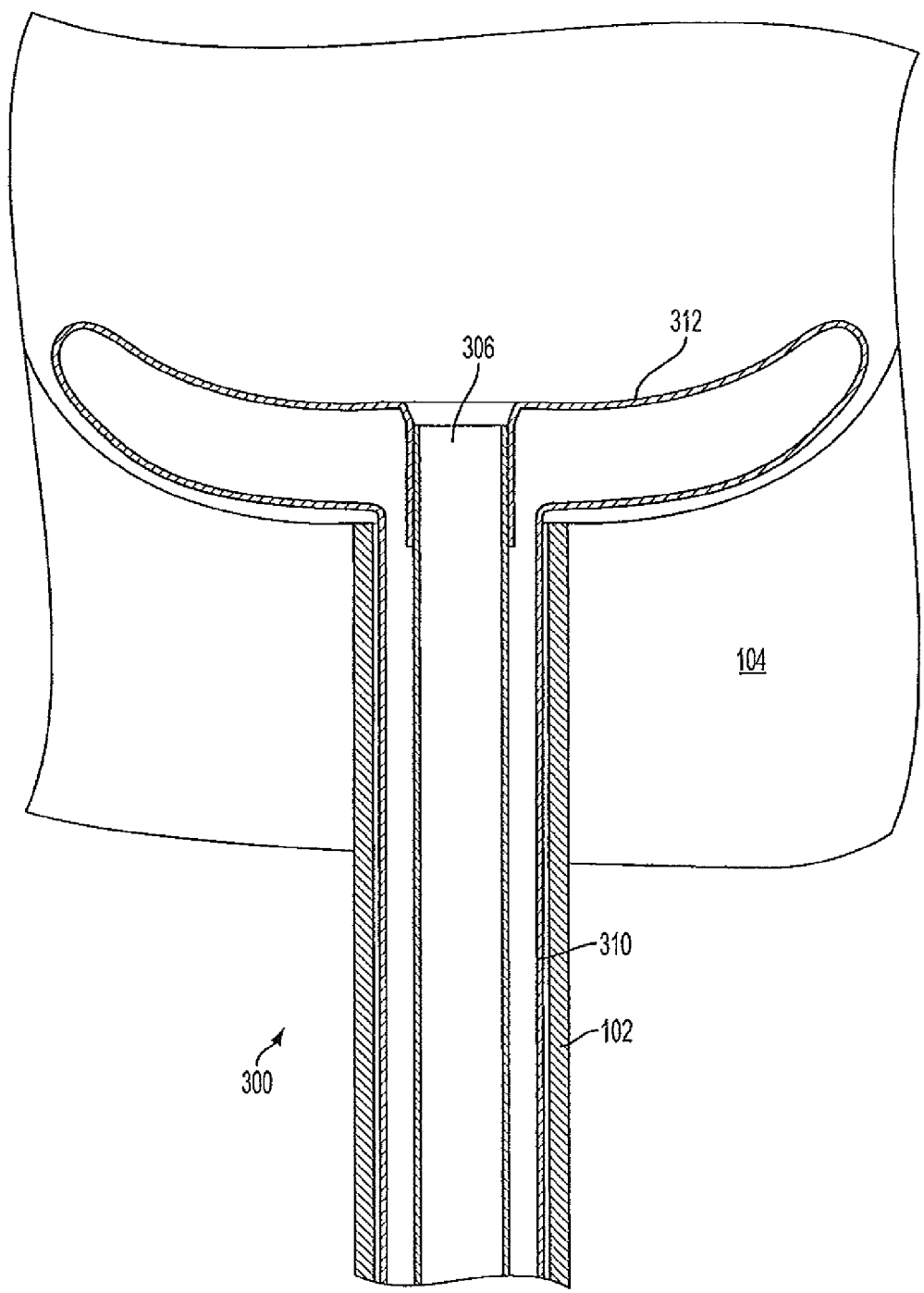
FIG. 15 is a cross-sectional side elevation view of a portion of the device of FIG. 13, showing the anchor member expanded to block implant material from extruding out of the annulus opening and to anchor the device in place.

With continued reference to FIG. 13, device 300 is shown being introduced through an opening in annulus 104 by way of cannula 102. Device 300 can be advanced beyond the end of cannula 102, as indicated in FIG. 14, to expose a distal portion of blocking component 310. The exposed portion of blocking component 310 can be inflated into a catheter balloon 312, as shown in FIG. 15. With catheter balloon 312 anchoring device 300 in place and sealing the opening in annulus 104, catheter 306 can be used to introduce instruments to inject implant material into the interior of annulus 104, much as described above.

Figure 16:
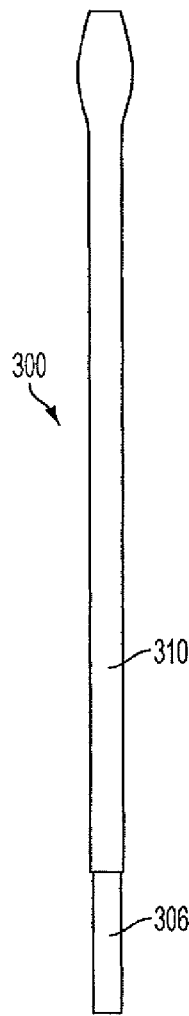
FIG. 16 is a side elevation view of the device of FIG. 13, showing the anchor member in an unexpanded state.
Figure 17:
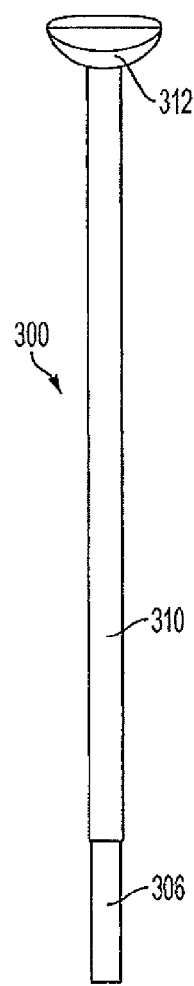
FIG. 17 is a side elevation view of the device of FIG. 13, showing the anchor member in an expanded state.
Figure 18:
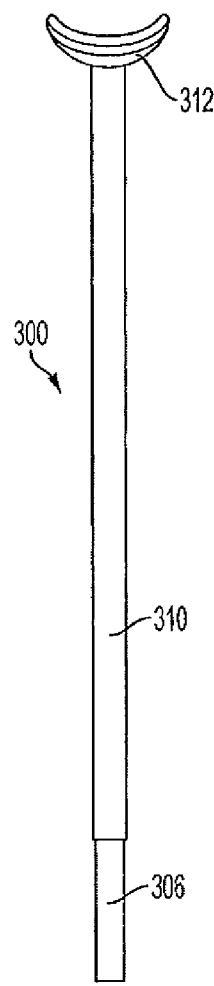
FIG. 18 is a side elevation view of the device of FIG. 13, showing the anchor member in an expanded state with the distal end concave as though depressed by implant material when inside a disc annulus.
Figure 19:
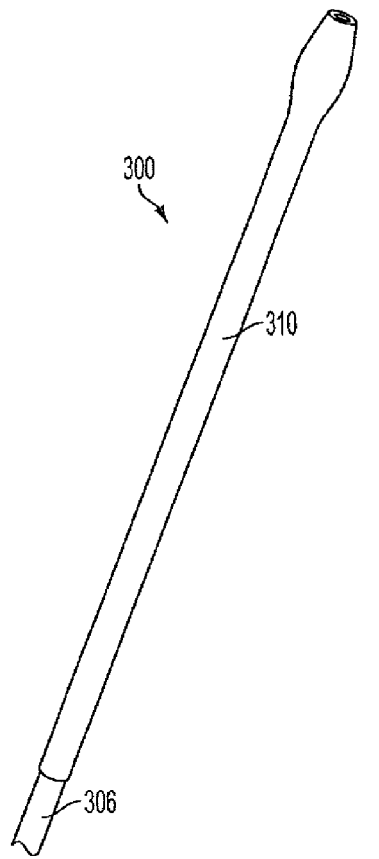
FIGS. 19-21 are perspective views of the device of FIG. 13, showing the anchor member in the states of FIGS. 16-18, respectively.
Figure 20:
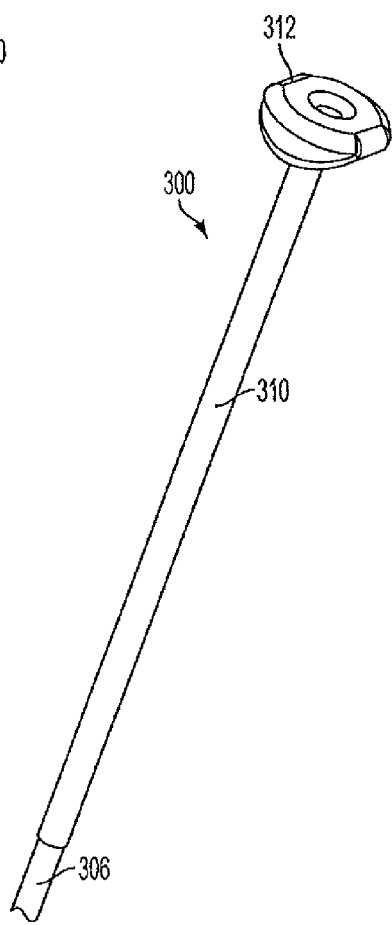
Figure 21:
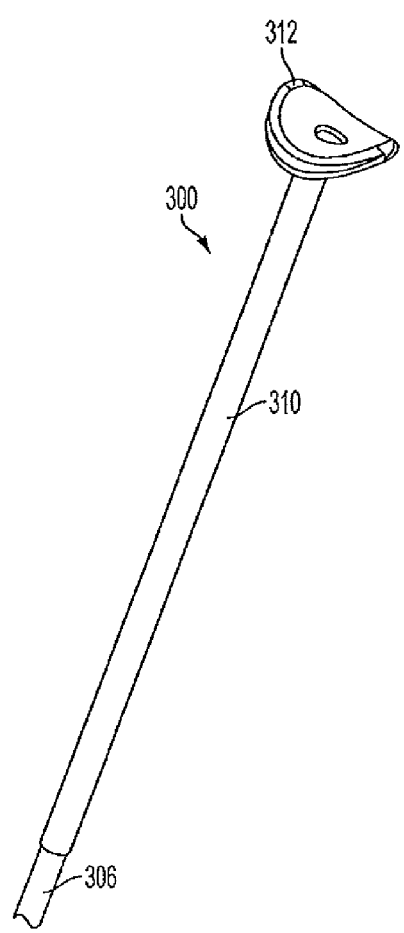

FIG. 16 shows device 300 without a cannula and in the deflated state. In FIG. 17, the shape of catheter balloon 312 is shown as it can appear inflated in a disc annulus prior to injection of implant material. Once the implant material has been injected, it will press against catheter balloon 312, resulting in a catheter balloon shape like that shown in FIG. 18, for example. FIGS. 19-21 show perspective views of the same states of device 300 as shown in FIGS. 16-18, respectively.

The devices and methods described above have been provided in the exemplary context of open discectomy procedures where the discectomy opening is sealed to prevent re-herniations and to resist further disc degeneration. Those skilled in the art will readily appreciate that the methods and devices described above can readily be used for nucleotomy or discectomy, open or percutaneous.

Those skilled in the art will also readily appreciate that the methods and devices described above can also be applied or adapted to any other suitable procedure without departing from the spirit and scope of the invention. For example, vertebroplasty involves a placement of a large needle through a percutaneous or open approach into a vertebral bone that is fractured. Cement is injected to stabilize the bone and reduce pain. Cement leakage is a problem with this approach. A similar approach is Kyphoplasty, which involves the application of a needle with a balloon which is filled with water and expanded to create a void in a broken bone. This allows for correction after a compression fracture has occurred. Kyphoplasty allows for placement of a viscous cement which has a tenancy to migrate because less pressure is needed with the void and more viscous nature of the cement. In these additional exemplary procedures, the devices and methods described herein can readily be applied to anchor catheters and/or to seal or block surgical openings to prevent unwanted migration of implant material. Moreover, those skilled in the art will readily appreciate that the applications of the devices and methods described herein are not limited to spine related procedures, but can be readily adapted to any suitable procedures without departing from the spirit and scope of the invention.

The methods and systems of the present invention, as described above and shown in the drawings, provide methods and devices for delivery of spinal disc implants with superior device anchoring and blocking against extrusion of implant material. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A spinal disc implant delivery device comprising:
   a) a blocking component having opposed distal and proximal ends, the distal end of the blocking component including an anchor member configured and adapted for movement between an undeployed position in which the anchor member can pass into and out of an opening in a disc annulus, and a deployed position in which the anchor member anchors the blocking component to the opening of the disc annulus, wherein in the deployed position, the anchor member is configured to prevent extrusion of implant material from the opening of the disc annulus, wherein the anchor member is further configured and adapted for movement from the undeployed position to the deployed position by advancing the anchor member toward the disk annulus; and
   b) an implant delivery needle located radially within the blocking component and having opposed proximal and distal ends, the needle being configured to be advanced independently of and distally beyond the blocking component and deliver implant material from the distal end thereof to an interior of the disc annulus.

2. A spinal disc implant delivery device as recited in claim 1, wherein the implant delivery needle is moveable relative to the blocking component in an axial direction.

3. A spinal disc implant delivery device as recited in claim 1, wherein the anchor member includes a mesh portion that is biased toward the deployed position.

4. A spinal disc implant delivery device as recited in claim 1, further comprising a pressure sensor mounted to at least one of the blocking component and the implant delivery needle.

5. A spinal disc implant delivery device comprising:
   a) a blocking component having opposed distal and proximal ends, the distal end of the blocking component including an anchor member configured and adapted for movement between an undeployed position in which the anchor member can pass into and out of an opening in a disc annulus, and a deployed position in which the anchor member anchors the blocking component to the opening of the disc annulus, wherein in the deployed position, the anchor member is configured to prevent extrusion of implant material from the opening of the disc annulus, wherein the anchor member is further configured and adapted for movement from the undeployed position to the deployed position by advancing the anchor member toward the disk annulus; and
   b) an implant delivery needle located radially within the blocking component and having opposed proximal and distal ends, the needle being configured to deliver implant material from the distal end thereof to an interior of the disc annulus,
   wherein the anchor member includes a membrane lining the mesh portion to prevent extrusion of implant material through the mesh portion.

6. A spinal disc implant delivery device comprising:
   a) a blocking component having opposed distal and proximal ends, the distal end of the blocking component including an anchor member configured and adapted for movement between an undeployed position in which the anchor member can pass into and out of an opening in a disc annulus, and a deployed position in which the anchor member anchors the blocking component to the opening of the disc annulus, wherein in the deployed position, the anchor member is configured to prevent extrusion of implant material from the opening of the disc annulus, wherein the anchor member is further configured and adapted for movement from the undeployed position to the deployed position by advancing the anchor member toward the disk annulus; and
   b) an implant delivery needle located radially within the blocking component and having opposed proximal and distal ends, the needle being configured to deliver implant material from the distal end thereof to an interior of the disc annulus,
   wherein the anchor member includes a catheter balloon configured and adapted to inflate into the deployed position within an interior of a disc annulus to prevent withdrawal of the blocking component from the disc annulus.

7. A spinal disc implant delivery device as recited in claim 4, wherein the blocking component includes a catheter having opposed proximal and distal ends, and wherein the catheter balloon is attached to the catheter by a ferrule mounted to the catheter.

8. A spinal disc implant delivery device as recited in claim 7, wherein the ferrule is mounted at the distal end of the catheter.

9. A spinal disc implant delivery device as recited in claim 4, wherein the blocking component includes a catheter having opposed proximal and distal ends, and wherein the catheter balloon includes a flexible tube with a distal end thereof folded radially inward and overlapping a radially outward portion of the flexible tube, the distal end of the flexible tube being mounted to the catheter proximate the distal end of the catheter.

* * * * *